United States Patent [19]

Wilder

[11] Patent Number: 4,695,456
[45] Date of Patent: Sep. 22, 1987

[54] METHOD FOR ALLEVIATING SKIN IRRITATION BY FORMULATIONS CONTAINING SUPEROXIDE DISMUTASE

[75] Inventor: Martin S. Wilder, Amherst, Mass.

[73] Assignees: Centerchem, Inc., Tarrytown, N.Y.; Pentapharm AG, Basel, Switzerland

[21] Appl. No.: 666,677

[22] Filed: Oct. 31, 1984

[51] Int. Cl.$^4$ ............................................ A61K 37/48
[52] U.S. Cl. .................................................. 424/94.5
[58] Field of Search .......................................... 424/94

[56] References Cited

U.S. PATENT DOCUMENTS 4,129,644 12/1978 Kalopissis et al. .................... 424/94
4,563,349 1/1986 Miyata et al. ........................ 435/189

OTHER PUBLICATIONS

Yakurigaku—Chem. Abst., vol. 102 (1985) p. 12207k, patent issue date Sep. 6, 1984.
Oyanagui—Chem. Abst., vol. 95 (1981) p. 180823p.
McCord et al.—Chem. Abst., vol. 94 (1981) p. 172739e.

*Primary Examiner*—Sam Rosen
*Attorney, Agent, or Firm*—Kenyon & Kenyon

[57] ABSTRACT

This invention discloses use of superoxide dismutase (SOD) as an agent for the protection of the skin against inflammatory reactions associated with chemical irritation and acne. Topical application of SOD in a formulation attenuates dermal injury associated with the induction of reactive oxygen species by a wide variety of chemical irritants, associated with inflammation, and associated with acne.

24 Claims, No Drawings

METHOD FOR ALLEVIATING SKIN IRRITATION BY FORMULATIONS CONTAINING SUPEROXIDE DISMUTASE

BACKGROUND OF THE INVENTION

Adverse skin reactions caused by chemical irritants are common among humans. Many of these irritants are constituents of cosmetic products while others are noxious industrial chemicals including organic solvents and caustic materials. In view of this wide spectrum of irritants, several physiologically injurious mechanisms have been postulated as underlying the adverse reactions. To deal with these possibilities, researchers have developed several classes of antiirritants.

According to Goldemberg, (In "Principles of Cosmetics for the Dermatologist", Phillip Frost and Stephen N. Horwitz, Eds., The C. V. Mosby Company, St. Louis, Mo. p.34; Goldemberg, R. M., 1979, *J. Soc. Cosmet. Chem.*, 30:415) an antiirritant could be reacted with the irritant chemical to complex the irritant or change its nature so that it no longer irritates. Alternatively, the reactive skin sites can be blocked so that they no longer react with irritants. Additionally, a heavy layer of grease which is positioned between the skin and chemical irritants may also be used. Finally, the problem of irritation may be attenuated by extreme dilution of the irritant.

In general it is possible that chemical irritant injury of cells may be associated with the generation of toxic, free radicals. For example, when insulin secreting cells are exposed in vitro to solutions containing alloxan, hydroxyl radical is produced extracellularly with ensuing manifestations of plasma membrane damage. (Fischer, L. J. and Harmon, A. W. 1982, In "Pathology of Oxygen," Anne P. Auter. Ed. Academic Press. N.Y. p. 261). Paraquat, a pyrazine derivative which is easily reduced to a relatively stable free radical, is believed to augment the production of superoxide by chloroplasts and lung microsomes, and this is probably one reason for paraquats lethality in both plants and animals. (Hassan, H. M. and Fridovich, I., 1977, *J. Bacteriol*, 130:805; *J. Bacteriol*, 132:505). Also, carrageenan-induced and kaolin-induced inflammation in the rat has been suppressed by the use of the oxygen free radical scavenger, superoxide dismutase (Huber, W. and Saifer, M. G. 1977, In "Superoxide and Superoxide Dismutases", A. M. Michelson, J. M. McCord, and I. Fridovich, Eds. Academic Press, N.Y., 1977, p. 517; Oyanagui, Y., 1976, *Biochem., Pharmacol*, 25:1465).

It is known that biological reduction of molecular oxygen is accompanied by the production of reactive free-radical intermediates. The complete reduction of a molecule of oxygen to water requires four electrons, and in a sequential univalent process several intermediates are encountered. These are the superoxide anion-radical, hydrogen peroxide, and the hydroxyl radical, and such intermediates are too reactive to be well tolerated within living systems (Czapski, G. 1971, *Annu. Rev. Phys. Chem.*, 22:171).

The superoxide anion radical, hydrogen peroxide and the hydroxyl radical which may be generated enzymatically or photochemically, are known to inactivate microorganisms, induce lipid peroxides, damage membranes and kill cells (Fridovich, I., 1982, In "Pathology of Oxygen," Anne P. Autor., Ed., Academic Press, Inc., New York.,p. 1). A primary defense against toxic oxygen radicals is provided by enzymes that catalytically scavenge the intermediates of oxygen reduction. For example, the superoxide anion radical may be eliminated by superoxide dismutases, which catalyze its conversion to hydrogen peroxide and oxygen.

There are indications that superoxide is not itself the species that causes injury to cells but may be the precursor of a more potent oxidant, the hydroxyl radical, the generation of which depends on the simultaneous presence of hydrogen peroxide. (Haber, R. and Weiss, 1934, *J. Proc. Roy. Soc. London*, Ser. A., 147:332). Thus, it seems that the greatest danger posed by superoxide is its interaction with hydrogen peroxide or with organic peroxides, which can generate a highly reactive entity like hydroxyl radical that can then attack essential cell components.

Several reports have appeared presenting data that the enzyme, superoxide dismutase (SOD), may function at the level of the skin. For example, two groups of researchers hav shown that systemic administration of SOD to rats will inhibit the reverse passive Arthus reaction in the skin (Petrone et al., 1980, *Proc. Natl. Acad. Sci.*, 77:1159; Parellada, P. and Planas, J. M., 1978, *Biochem. Pharm.*, 27:535). Further, treatment of facial lesions in patients with Crohn's disease with a topical application of liposomes containing superoxide dismutase was followed by marked improvement with a diminution of swelling (Michelson, A. M., 1982. In "Pathology of Oxygen", Anne P. Autor, Ed., Academic Press, N.Y., p. 277). Kalopissis et al. (U.S. Pat. No. 4,129,644 "Protecting Skin and Hair with Cosmetic Compositions Containing Superoxide Dismutase") claim that representative superoxide dismutase extracts of marine bacteria protect the keratinic structure of the skin of rats from the effects of intraperitoneally injected testosterone propionate. They additionally claim that topical application of a cream containing SOD would protect the skin from the harmful effects of ultra-violet rays produced by irradiation of human subjects with a Xenon, U.V. Solar Simulator. Other workers have shown that topical administration of a low molecular weight lipophilic copper coordination complex with superoxide dismutase-mimetic activity inhibits certain phorbol ester-induced biochemical and biological responses associated with carcinogenesis as well as the number of developing papillomas (Kensler, T. W., Bush, D. M., Kozumbo, W. J., 1983, *Science*, 221:75). Superoxide radical scavenging agents have also been used to protect rabbit cornea against alkali injury. (Nirakari et al., 1981, *Arch. Ophthalmol.*, 99; 886). The unique avascularity of the cornea suggests that such oxygen radicals participate directly in the promotion of the corneal ulceration.

Until the present invention, however, agents for scavenging the intermediates of the biological reduction of oxygen have not been used to protect the skin from the deleterious action of diverse classes of chemical irritants. Moreover, there is no evidence indicating that the toxic dermal manifestations induced by a wide array of chemical irritants of the skin can be abrogated through the use of a single biological agent. Current knowledge of skin irritation requires use of divergent protective approaches as explained above. Finally, scavenger agents have not been suggested for use in the control of dermal inflammatory reactions including acne.

Accordingly, it is an object of the invention to provide a general method for prevention or alleviation of chemical irritation of the skin through the topical use of a single biological agent in combination with a suitable carrier or vehicle. Another object is the use of such a biological agent which scavenges free radical intermediates of biological oxidation-reduction reactions. It is a further object to use such an agent for the general control of dermal inflammation and acne. Other objects include the formulation of creme, gel, lotion and liquid preparations for the skin which will protect it from injury by diverse chemical irritants and will prevent or alleviate inflammation and acne.

SUMMARY OF THE INVENTION

These and other objects are achieved by the present invention which is directed to a topical formulation for the protection of the skin against chemical irritation and a method for preventing or alleviating skin irritation, general skin inflammation and acne by employing such a topical formulation.

The formulation is a suitable, cosmetic or dermatologicly acceptable, non-toxic, non-allergenic carrier containing such an amount of SOD that with one application of the formulation at least about 1 CIU, preferably at least about 2.5 CIU, more preferably about 10 to 1000 CIU's of purified superoxide dismutase (hereinafter SOD) are applied per $cm^2$ of treated skin. It appears that this minimum amount of about 1 CIU of SOD, preferably at least about 2.5 CIU of SOD, and more preferably about 10 to 1000 CIU of SOD per $cm^2$ of skin is important for the achievement of the protection against or alleviation of the injury to skin caused by diverse classes chemical irritants of the skin. This minimum amount of SOD also prevents or alleviates skin inflammation and acne. The SOD used for cosmetic or dermatologic formulation can be in the form of tissue or cell extracts containing preparations provided that the appropriate adjustments in SOD concentration are made.

The method for alleviation or treatment of skin irritation, inflammation and acne is topical administration to the skin of a cosmetic or dermatologic formulation containing at least about 0.026 percent purified SOD with a specific activity of about 3800 CIU/mg protein relative to the total weight of the formulation. It appears that this percentage corresponding to about 1 CIU/$cm^2$ of skin is the minimum effective amount which will protect against or alleviate many deleterious manifestations of the skin. In particular, the method of the invention can be used to protect from or alleviate the pathological effects to the skin which are caused by many chemical irritants. The method may also be used to prevent or alleviate inflammation of the skin caused by an indeterminant vector. Further, the method may be used to prevent or alleviate acne.

DETAILED DESCRIPTION OF THE INVENTION

This present invention is inter alia based upon the belief that chemical initiation of dermal injury, concomitant inflammatory responses and acne vulgaris are associated with the production of oxygen-derived metabolites which can be detoxified by topical application of superoxide dismutase. However, this belief is not meant to be limiting of the invention which is set forth in the text herein.

Tissue injury, whether it be mechanical, chemical, toxic or thermal, produces a local reaction which is usually referred to as inflammation. In association with this, changes occur in the plasma and cells of the blood as part of a general reaction to injury. These changes affect the local reaction and are often concerned with defense mechanisms such as phagocytosis, hemostasis, and repair.

Tissue injury may result from either the direct effects of the pathologic chemical agent or as a consequence of an inflammatory cell influx. In this regard, it has been found that superoxide dismutase can either prevent direct chemical injury as well as subsequent deleterious manifestations caused by inflammatory consequences.

Accordingly, the present invention employing a topical formulation of SOD can function as a single biological agent for the protection of the skin against diverse classes of chemical irritants. These classes of chemical irritants include inorganic and organic peroxides, inorganic and organic acids including for example long chain fatty acids and acnegenic fatty acids, inorganic and organic bases, agents which produce free radicals including nitroso compounds, heterocyclic compounds organic peroxides and the like, chlorine, astringents, keratinizing agents, skin sloughing agents, para-aminobenzoic acid derivatives and the like.

It is believed that superoxide plays a key role in the initiation and perpetuation of granulocyte-mediated inflammation. The mechanisms appear to involve the reaction of superoxide with a plasma protein to form a potent chemotactic factor responsible for the initial accumulation of granulocytes at the site of the developing lesion. Further, the ability of macrophages and neutrophils to injure cells and host tissues appears to be dependent upon the production of oxygen-derived free radicals and their metabolites and the ability of the target cells and tissues to detoxify the reactive species. The balance between the production and catabolism of oxidants by cells and tissues is important for the maintenance of their biologic integrity. In this regard, release of superoxide intermediates into extracellular fluids would be largely unopposed by SOD since SOD is ordinarily not present in such fluids. Thus, inflammation appears to be correlated with oxygen metabolite induced cellular injury. Superoxide dismutase plays an important role in the defense of superoxide mediated toxicity. Accordingly, it is believed that topical application of SOD can protect skin against direct chemical injury and subsequent deleterious inflammatory reactions associated with superoxide generating systems.

Surface lipids of man contain appreciable amounts of free fatty acids formed by the action of bacterial lipases on the triglycerides of sebum. Since these free fatty acids are very irritating when injected intracutaneously, they are thought to be implicated in acnegenesis, and a major hypothesis of comedogenesis has evolved concerning their role. The free fatty acid hypothesis proposes that under the driving stimulation of androgenic hormones, human sebaceous glands enlarge with resulting increased production of sebaceous lipids. The major sebaceous lipid component, triglycerides is hydrolyzed in the sebaceous follicle by bacterial esterases and lipases. Certain free fatty acids of chain lengths between $C_{12}$ and $C_{18}$ act as irritants and/or comedogenic agents to damage the wall of the sebaceous follicle leading to subsequent follicular rupture and extrusion of keratinous debris, lipids and bacteria into the surrounding dermis producing the initial inflammatory events associated with clinical acne. Accordingly, the present invention protects the dermis against the changes induced by acnegenic fatty acids produced by bacterial lipolysis of the follicle content which induces the production of toxic oxygen intermediates.

Based on these principles, the formulation of the present invention protects the skin against injury caused by chemical irritants, against inflammation and can substantially prevent or alleviate the untoward conditions of acne vulgarus and associated dermal abcesses such as boils, carbuncles, pustules and the like.

According to the invention, the topical formulation can be prepared with common cosmetic, non-toxic, non-allergenic carriers for use in skin cremes, lotions, sprays, liquids, emulsions, cleansing preparations and the like. For the purposes of achieving protection from or alleviation of the irritation and inflammation of the skin by the foregoing classes of chemical irritants, and for achieving protection from, or alleviation of, dermal inflammation and acne the minimum concentration of SOD present in the topical formulation preferably should be at least about 0.026 weight percent of a SOD preparation with a specific activity of about 3800 CIU/mg protein relative to the total weight of the composition. It appears that protection against some classes of irritants is afforded below this concentration, but attenuation of injury induced by other chemicals is diminished. Thus when the minimum concentration of SOD is used in the formulation of the invention, skin wheal and reddening as well as more potent indications of dermal inflammation such as swelling, edema and leukocyte infiltration are lessened compared with the intensities of these pathological manifestations which appear in controls or when less than the minimum concentration of SOD is employed.

A typical formulation prepared according to the present invention will contain from about 50 to 100% water, from about 0 to 20% organic polyol, from about 0 to 30% $C_{12}$ to $C_{18}$ fatty acid ester, from about 0 to 30% of an oil or paraffin, from about 0 to 20% of a suitable ionic or nonionic emulsifier base and from at least about 0.026% SOD with a specific activity of about 3800 CIU/mg protein wherein the weight percentages are relative to the total weight of the composition. Additional ingredients may be added according to the understanding of those familiar with the cosmetic art in order to vary the texture, consistency, viscosity, appearance, weight, etc. of the formulation. Its physical character may be that of a semi-solid paste, gel, solution, emulsion, lotion, liquid, spray, creme and the like and these ingredients may be employed to produce such adjustment of the physical character. These additional ingredients include inter alia emulsifying agents such as nonionic ethoxylated and or nonethexylated surfactants, fatty alcohols, fatty acids, organic or inorganic bases, preserving agents, wax esters, steroid alcohols, triglyceride esters, phospholipids such as lecithin and cephalin, polyhydric alcohol esters, fatty alcohol ethers, hydrophilic lanolin derivatives, hydrophilic beeswax derivatives, hydrocarbon oils and such as palm oil, coconut oil, mineral oil, carnuba wax, cocoa butter waxes, silicone oils, pH balancers such as borax, gum thickeners such as acacia, tragacanth, guar, alginate and the like, cellulose derivatives such as methyl cellulose, sodium carboxymethyl cellulose, hydroxyethyl- or hydroxypropyl-cellulose and the like, perfume and the like.

Use of the formulation of the invention will generally be effective under the following conditions of application; however, the use may be varied on an individual basis in order to establish the most effective conditions for the individual.

Generally, the formulation may be applied to the skin at least 5 to 10 minutes before potential exposure to a chemical irritant. The application may be made over the entire area of the skin which could be exposed and the amount of formulation applied should be calculated to deliver at least about 1 CIU (CIU is defined as cytochrome inhibition unit), preferably at least about 2.5 CIU of SOD, and more preferably about 10 to 1000 CIU of SOD or its equivalent per square cm of skin. In this fashion, the minimum amount of SOD will be applied to the skin.

Post exposure to irritant treatment will follow the same procedures. The course of control of inflammation and acne will be alleviated in this fashion but application also will be made concomitant with the onset of inflammatory symptoms.

In a typical application, a skin creme, gel or lotion containing at least about 0.026 weight percent of SOD with a specific activity of about 3800 CIU/mg protein can be applied at an area concentration of about 2 to 20 mg per square cm of skin. In practical terms, this area concentrations of creme, gel or lotion may be achieved by application of about 0.4 to 4 drops per 10 sq cm on the basis that each drop is about 0.05 ml or 50 mg of formulation.

The invention will now be illustrated by the following examples which delineate some of the foregoing features of the invention. The examples are not meant as limiting, however.

EXPERIMENTAL PROTOCOLS FOR THE EXAMPLES

The following examples illustrate the protective effects of topical application to the skin of either purified superoxide dismutase concentrate or partially purified SOD isolated as extract from blood, liver or other suitable organ of animals, from microorganisms or suitable cell cultures.

The used purified commercial preparation of SOD was assayed by its ability to inhibit the reduction of cytochrome C (cytochrome inhibition unit), hereafter CIU, pursuant to the method of McCord, J. M. and Fridovich, I., 1968, *J. Biol. Chem.*, 243:5753. Cytochrome c is readily reduced by superoxide and serves as a useful indicator. SOD acts to inhibit cytochrome c reduction because the enzyme catalyzes the dismutation of superoxide and competes with cytochrome c for the available superoxide generated by the xanthine, xanthine oxidase system.

Superoxide dismutase in extracts was assayed by its ability to inhibit the solution autooxidation of an aqueous pyrogallol solution at pH 8 (pyrogallol inhibition unit) hereafter PIU in which the superoxide anion radical acts as a chain propagating species. In such situations, SOD will, by scavenging the superoxide anion radical, shorten the reaction chains and so decrease the overall rate of that autooxidation of pyrogallol. This assay is used pursuant to the method of Marklund, S. and Marklund, G., 1974, *Eur. J. Biochem.*, 47:469. For these determinations, autooxidation activity was converted to cytochrome C inhibition units (1 CIU corresponds to about 2.5 PIU).

For each experiment, 0.05 ml of either an aqueous solution of commercial SOD (purified) with an activity of about 5000 CIU/ml or of bovine SOD extract (semipure) with an activity of about 5000 PIU/ml was applied to the lower third of the shaven ear of either New Zealand White or French lop rabbits. The enzyme preparation was allowed to set for approximately 5 minutes and 0.05 ml to 0.1 ml of the chemical irritant was added to the same area of approximately 1.5 cm=2.25 sq cm in size. After 5 minutes, 0.05 ml of SOD solution or extract was reapplied to the same site. As a oontrol, the other ear was utilized substituting phosphate buffered saline (PBS) for SOD.

Erythema was recorded two hours after application of the chemical irritant and scored as follows: 1+slight-/minimal but definite redness; 2+moderate redness; 3+considerable redness; 4+intense redness; 5+maximal redness. Results are expressed as erythema initiated by irritant chemical in animals treated with superoxide dismutase and erythema initiated by same irritant chemical but treated with PBS as control. The protective index represents the diminution in erythema and is expressed as the difference between the scores of the erythematous reaction of the PBS-treated control side minus that of the SOD, treated side. For further verification, descriptions are presented of other pertinent inflammatory and pathologic manifestations which develop over a four day period.

In the Examples 1-9 PSOD indicates purified, aqueous superoxide dismutase solution with an activity of about 5000 CIU/ml while SPSOD denotes semi-pure SOD tissue extract preparation with an activity of 5000 PIU/ml used for testing. All irritants were tested on at least five different rabbits and each experiment on any given animal was repeated four times. The data presented represent the average of these experiments.

Experimentation with dose responses reveals that effective quantities as low as from about 1 CIU of SOD per sq. cm. of skin initiates dermal protection against chemical irritation.

EXAMPLE 1

| Irritant Chemical | Experiment | SPSOD/Control | Protective Index |
| --- | --- | --- | --- |
| Sodium Lauryl | 1 | 2+/3+ | 1 |
| Sulfate 20% (w/v) | 2 | 1+/2+ | 1 |
| aqueous solution | 3 | 0/3+ | 3 |
| | 4 | 3+/4+ | 1 |
| | 5 | 0/2+ | 2 |
| | 6 | 0/1+ | 1 |
| | 7 | 1+/3+ | 2 |

After 30 minutes, erythema is markedly greater in the PBS control ear when contrasted with the SP SOD treated site. At 24 hours, the SPSOD ear displays minimal erythema (0−1+) with tiny scab-like formations around small follicles which cover approximately 1/5 the SPSOD application area. In four days, one occasionally obsreves a small raised scab covering approximately 1/10 the application diameter. In addition to erythema observed at 30 min in the control ear, there is considerable edema at 80 min. Edema and erythema persist and continue to spread beyond the area of SPSOD application with the development of discoloration surrounding the follicles at this interval. After 24 hours, erythema remains while edema begins to subside. Brown scab-like formations around the follicles covering 75% of the application area become evident. After four days, raised scab formation persists over 75% of the area of application in the control ear.

EXAMPLE 2

| Irritant Chemical | Experiment | PSOD/Control | Protective Index |
| --- | --- | --- | --- |
| Sodium Lauryl | 1 | 0/3+ | 3 |
| Sulfate 20% (w/v) | 2 | 0/2+ | 2 |
| aqueous solution | 3 | 2+/3+ | 1 |
| | 4 | 3+/4+ | 1 |
| | 5 | 0/2+ | 2 |

Thirty minutes after applicaion of PSODS, erythema was markedly greater in the PBS-control ears when contrasted with either the PSOD or SPSOD treated sites. At 24 hours, the SOD ears displayed minimal erythema with tiny scab-like formations around small follicles which covered approximately 1/5 the SDS application area. After four days, one occasionally observed a small raised scab covering approximately 1/10 the application diameter. In addition to the erythema observed at 30 min in the control ears, some animals exhibited considerable edema at 80 min. Edema and erythema persisted and continued to spread beyond the area of PSOD application with the development of discoloration surrounding the follicles at this interval. After 24 hours, erythema remained while edema began to subside. In some rabbits, brown scab-like formations around the follicles covering 75% of the application area became evident. After four days, raised scab formation persisted over 75% of the area of PSOD-application in the control ears.

EXAMPLE 3

| Irritant Chemical | Experiment | PSOD/Control | Protective Index |
| --- | --- | --- | --- |
| Lauric Acid | 1 | 2+/3+ | 1 |
| 50% (w/v) in | 2 | 1+/2+ | 1 |
| n-propanol | 3 | 1+/3+ | 2 |
| | 4 | 2+/3+ | 1 |
| | 5 | 1+/2+ | 1 |
| | 6 | 3+/3+ | 0 |
| | 7 | 4+/4+ | 0 |
| | 8 | 1+/3+ | 2 |
| | 9 | 0/2+ | 2 |
| | 10 | 2+/2+ | 0 |
| | 11 | 2+/2+ | 1 |
| | 12 | 2+/4+ | 2 |
| | 13 | 2+/4+ | 2 |

Experiments with lauric acid indicated on the PSOD-ear a minimal erythema after 10 minutes and a 2+ erythema after 30 minutes which subsided at 24 hours. However, skin was scaling over approximately ⅓ the area of application with reddening surrounding folicles and visible under 10× magnification. In contrast, the control ear revealed a 2+ erythema reaction covering twice the area of application already after ten minutes and after 30 minutes, the erythematous reaction was considerable (3+). Although erythema was minimal after 24 hours, skin was scaling over ½ the area of application. Surrounding the region of scaling were large numbers of follicles with red scab-like formations. Additionally, in contrast to the PSOD treated ear, a darker and larger area of erythema was observed surrounding individual follicles. These observations are the expression for a much more severe inflammatory reaction of the control sites compared to the PSOD treated skin.

EXAMPLE 4

| Irritant Chemical | Experiment | SPSOD/Control | Protective Index |
|---|---|---|---|
| Cinnamaldehyde | 1 | 2+/3+ | 1 |
| 0.1% (v/v) in | 2 | 2+/4+ | 2 |
| methanol | 3 | 2+/4+ | 2 |
|  | 4 | 2+/2+ | 0 |

The prodominant difference observed between the SOD ears and the PBS-treated control ears was the more extensive erythematous reaction in the latter which persisted to a larger extent than on the SPSOD-treated ears.

EXAMPLE 5

| Irritant Chemical | Experiment | SPSOD/Control | Protective Index |
|---|---|---|---|
| Benzoyl Peroxide | 1 | 1+/2+ | 1 |
| 5% (w/v) in | 2 | 3+/4+ | 1 |
| ethyl ether |  |  |  |

EXAMPLE 6

| Irritant Chemical | Experiment | PSOD/Control | Protective Index |
|---|---|---|---|
| Benzoyl Peroxide | 1 | 3+/4+ | 1 |
| 5% (w/v) in | 2 | 2+/4+ | 1 |
| ethyl ether |  |  |  |

In SOD-(SPSOD) treated ears, the inflammatory response developed slowly with considerable erythema eveloping 75 and 100% of the application diameter after 24 and 48 hours respectively. In marked contrast, the PBS-treated control ears displayed intense redness at 24 hours with erythema spreading to twice the diameter of the application site at 48 hours.

EXAMPLE 7

| Irritant Chemical | Experiment | PSOD/Control | Protective Index |
|---|---|---|---|
| Sodium Hydroxide (aqueous solution) |  |  |  |
| 1% (w/v) | 1 | 1+/2+ | 1 |
| 4% (w/v) | 2 | 0/1 | 1 |
| 5% (w/v) | 3 | 3+/4+ | 1 |

EXAMPLE 8

| Irritant Chemical | Experiment | SPSOD/Control | Protective Index |
|---|---|---|---|
| Sodium Hydroxide (aqueous solution) |  |  |  |
| 1% (w/v) | 1 | 4+/5+ | 1 |
| 4% (w/v) | 2 | 2+/2+ | 0 |
| 5% (w/v) | 3 | 2+/3+ | 1 |

In examples 7 and 8, erythematous reactions developed more rapidly and with greater intensity in the PBS-treated controls. Following application of sodium hydroxide, SOD-treated animals revealed slight edema 45 minutes after application with inflammatory manifestations subsiding at 90 minutes. There was generally no visible reaction after 24 hours. In contrast, the PBS-treated controls showed a rapidly developing and spreading erythematous reaction extending to twice the application diameter after 30 minutes. There was more intensive edema in the area of application which progressively intensified at 90 minutes. After 24 hours moderate erythema, scab-like eruptions with occasional dermal necrosis surrounding the perimeter of the application site was observed with the controls.

EXAMPLE 9

| Irritant Chemical | Experiment | PSOD/Control | Protective Index |
|---|---|---|---|
| Eugenol | 1 | 1+/1+ | 0 |
| 75% (v/v) | 2 | 1+/2+ | 1 |
| in methanol | 3 | 2+/4+ | 2 |

The predominant difference observed between the PSOD ears and the PBS-treated controls were the intensity and size of erythema. The controls generally revealed more erythema covering a larger area of the application diameter, than the PSOD-treated ears.

Additional tests were performed in the same manner as described before, using formaldehyde solution, retinoic acid and squalene as chemical irritant which showed similar results of reduced erythematous reactions on those ears treated with SOD-preparations in comparison to the PBS-treated controls.

For skin care products, SOD can be dispersed in non-toxic, non-allergenic topical cremes such as the cremes or lotions described below or their equivalents.

EXAMPLE 10

A Creme Formulation

A protective skin care SOD formulation of the type of an oil in water (o/w) emulsion cream having the following composition can be prepared.

3.0% of polyoxyethyleneglyceryl monostearate
2.0% of glyceryl distearate
3.0% of cetyl alcohol
6.0% of stearic acid
10.0% of isopropyl myristate
5.0% of fatty acid triglyceride ("Miglycol" 812)
0.2% of p-hydroxybenzoic acid ester as preserving agent ("Nipagin")
2.0% of glycerol
2.0% of propylene glycol
0.3% of preserving agent ("Germall" 115R)
5.0% of SOD-containing tissue extract with 20,000 PIU per ml
61.5% of demineralized water

EXAMPLE 11

A Lotion Formulation

A skin care lotion of the o/w type with addition of SOD-concentrate can be prepared in the following fashion 3.0% of polyoxyethyleneglyceryl monostearate
2.0% of sorbitan fatty acid ester
2.0% of cetyl alcohol
8.0% of isopropyl myristate
0.2% of p-hydroxybenzoic acid ester as preserving agent ("Nipagin")
2.0% of propylene glycol
0.3% of preserving agent ("Germall" 115R)

78.2% of demineralized water
3.0% of SOD-concentrate with 1,000,000 PIU/ml 0.5% of perfume.

EXAMPLE 12

A Gel

A fat and oil free skin care gel with addition of a SOD containing tissue extract can be prepared as follows.
1.4% w/w of Na-carboxymethyl cellulose as thickener
3.0% w/w of propyleneglycol
20.0% w/w of SOD-tissue extract with 20,000 PIU/ml
0.2% w/w of p-hydroxybenzoic acid as preservative
0.5% w/w of benzyl alcohol as preservative
74.9% w/w of water

EXAMPLE 13

A Solution

An aqueous, fat and oil free skin care solution with addition of a SOD containing cell extract can be prepared as follows.
71.7% w/w of demineralized water
10.0% w/w of propyleneglycol
0.3% w/w of preserving agent ("Phenonip" R)
0.5% w/w of Na-carboxymethyl cellulose
2.5% w/w of Na-citrate as buffer substance
10.0% w/w of native, soluble collagen as moisturizer
5.0% w/w of SOD-cell extract with 100,000 PIU/ml.

What is claimed is:

1. A method for the alleviation of dermal chemical irritation, dermal chemical inflammation or acne of the skin of a human, comprising applying at an area concentration of at least about 0.002 ml or 2 mg per square cm, a topical formulation containing a non-toxic, non-allergenic carrier and at least about 0.026 weight percent relative to the total weight of the formulation, of purified superoxide dismutase having an activity of at least about 3800 C.I.U./mg or an extract having an equivalent activity thereof, to the skin of said human having chemical irritation, inflammation or acne of the skin.

2. A method according to claim 1 wherein the skin of said human is affected by a chemical irritant.

3. A method according to claim 2 wherein the skin of said human is inflamed.

4. A method according to claim 1 wherein the skin of said patient is affected by acne.

5. A method according to claim 1 wherein said carrier is an aqueous gel or an aqueous solution.

6. A method according to claim 1 wherein said carrier is an oil in water or a water in oil emulsion.

7. A method according to claim 1 wherein said carrier is a dermatologically or cosmetically used water containing vehicle.

8. A method according to claim 1 wherein said carrier comprises about 50 to 100 weight % water, about 0 to 20 weight % polyol, about 0 to 30 weight % fatty acid ester and about 0 to 30 weight % oil or paraffin base and about 0 to 20 w % of an ionic or nonionic emulsifier, said weight percentages being relative to the total weight of the formulation.

9. A method for the alleviation of dermal chemical irritation, dermal chemical inflammation or acne of the skin of a human, comprising applying at an area concentration of at least about 0.002 ml or 2 mg per square cm, a topical formulation containing a non-toxic, non-allergenic carrier and an amount of superoxide dismutase (SOD) sufficient to deliver at least abvout 1 CIU of SOD per square cm.

10. A method according to claim 9 wherin the amount of SOD is calculated to deliver at least about 2.5 CIU of SOD per square cm.

11. A method according to claim 9 wherein the amount of SOD is calculated to deliver at least about 10 to about 1000 CIU of SOD per square cm.

12. A method according to claim 1 wherein the topical formulation is a dermatological or cosmetic skin creme or lotion.

13. A method according to claim 9 wherein the topical formulation is a dermatological or cosmetic skin creme or lotion.

14. A method for the alleviation of dermal chemical irritation, dermal chemical inflammation or acne of the skin of an animal, comprising applying at an area concentration of at least about 0.002 ml or 2 mg per square cm, a topical formulation containing a non-toxic, non-allergenic carrier and at least about 0.026 weight percent relative to the total weight of the fomulation, of purified superoxide dismutase having an activity of at least about 3800 C.I.U./mg or an extract having an equivalent activity thereof, to the skin of said animal having chemical irritation, inflammation or acne of the skin.

15. A method according to claim 14 wherein the skin of said animal is affected by a chemical irritant.

16. A method according to claim 15 wherein the skin of said animal is inflamed.

17. A method according to claim 14 wherein the skin of said patient is affected by acne.

18. A method according to claim 14 wherein said carrier is an aqueous gel or an aqueous solution.

19. A method according to claim 14 wherein said carrier is an oil in water or a water in oil emulsion.

20. A method according to claim 14 wherein said carrier is a dermatologically or cosmetically used water containing vehicle.

21. A method according to claim 14 wherein said carrier comprises about 50 to 100 weight % water, about 0 to 20 weight % polyol, about 0 to 30 weight % fatty acid ester and about 0 to 30 weight % oil or paraffin base and about 0 to 20 weight % of an ionic or nonionic emulsifier, said weight percentages being relative to the total weight of the formulation.

22. A method for the alleviation of dermal chemical irritation, dermal chemical inflammation or acne of the skin of an animal, comprising applying at an area concentration of at least about 0.002 ml or 2 mg per square cm, a topical formulation containing a non-toxic, non-allergenic carrier and an amount of superoxide dismutase (SOD) sufficient to deliver at least about 1 CIU of SOD per square cm.

23. A method according to claim 22 wherein the amount of SOD is calculated to deliver at least about 2.5 CIU of SOD per square cm.

24. A method according to claim 22 wherein the amount of SOD is calcuated to deliver at least about 10 to about 1000 CIU of SOD per square cm.

* * * * *